United States Patent [19]

Dwivedi et al.

[11] Patent Number: 5,283,247

[45] Date of Patent: Feb. 1, 1994

[54] ANTICONVULSANT SUBSTITUTED QUINAZOLONES

[75] Inventors: Chandradhar Dwivedi; Gary W. Omodt, both of Brookings, S. Dak.

[73] Assignee: Research Corporation Technologies, Inc., Tucson, Ariz.

[21] Appl. No.: 947,985

[22] Filed: Sep. 21, 1992

Related U.S. Application Data

[63] Continuation of Ser. No. 651,436, Feb. 6, 1991, abandoned.

[51] Int. Cl.$^5$ .................. A61K 31/505; C07D 471/04
[52] U.S. Cl. ...................... 514/259; 544/279; 544/284; 544/287; 544/290; 544/258
[58] Field of Search ............. 544/279, 284, 287, 290, 544/278; 514/259

[56] References Cited

U.S. PATENT DOCUMENTS

| | | | |
|---|---|---|---|
| 3,162,634 | 12/1964 | Klosa | 544/290 |
| 3,304,304 | 2/1967 | Claassen et al. | 544/287 |
| 3,414,573 | 12/1968 | Breuer et al. | 544/290 |
| 3,748,325 | 7/1973 | Somasekhara et al. | 544/284 |
| 3,755,581 | 8/1973 | Janiak | 514/259 |
| 4,276,295 | 6/1981 | Ishikawa et al. | 544/287 |
| 4,379,165 | 4/1983 | Clark | 424/324 |
| 4,638,014 | 1/1987 | Clark | 514/619 |

FOREIGN PATENT DOCUMENTS

| | | | |
|---|---|---|---|
| 0276826 | 8/1988 | European Pat. Off. | 544/284 |
| 0035123 | 11/1962 | Fed. Rep. of Germany | 544/287 |
| 139728 | 12/1968 | France . | |
| 997652 | 7/1965 | United Kingdom . | |
| 1183673 | 3/1970 | United Kingdom | 544/284 |
| 1297043 | 11/1972 | United Kingdom | 544/284 |

OTHER PUBLICATIONS

Premchand Karamchand, Chemical Abs. vol. 77, 1972 #126679m.
Ibid, Chemical Abstract. vol. 77, 1972 #140121e.
Maruyama, et al, Chemical Abstract, vol. 77, 1972 #101,653.
Ibid, Chemical Abstract, vol. 77, 1972 #101,654.
Bhaduri et al, "Indian Journal of Chemistry" vol. 18B pp. 443-448, 1979.
Kusters, H. C. et al, Poster Session, Aug. 13, 1990, Epilepsy: Anticonvulsants, Neuropharmacology and Neuropharmacology and Pathophsiology.
Karamchand Premchand, Chemical Abs., vol. 77, 1972 #126679m.
Karamchand Premchand, Chemical Abstract, vol. 77, 1972 #140121e.
Maruyama, et al., Chemical Abstract, vol. 77, 1972 #101653.
Maruyama, et al., Chemical Abstract, vol. 77, 1972 #101654.
Bhaduri et al., "Indian Journal of Chemistry" vol. 18B, pp. 443-448, 1979.

*Primary Examiner*—John M. Ford
*Assistant Examiner*—Y. N. Gupta
*Attorney, Agent, or Firm*—Dickstein, Shapiro & Morin

[57] ABSTRACT

Disclosed herein are substituted quinazolones and their $N^1$-oxide derivatives, methods of synthesizing such compounds, and methods of using them to treat or prevent convulsions in mammals. The substituted quinazolones are represented by the formula:

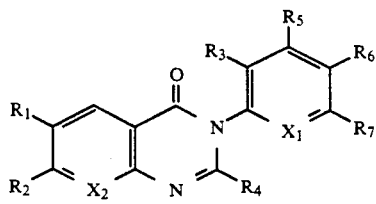

wherein $X_1$ is N, S, O, or CH, $X_2$ is N or CH, $R_1$ and $R_2$ are H, $NO_2$, or $NH_2$ except that when one of $R_1$ and $R_2$ is $NO_2$ or $NH_2$ the other is H, $R_3$ and $R_4$ are alkyl with 1-5 C atoms, and $R_5$, $R_6$, and $R_7$ are H or halogen, provided that when $X_1$ is N, S, or O, $X_2$ is CH.

18 Claims, No Drawings

ANTICONVULSANT SUBSTITUTED QUINAZOLONES

This application is a continuation of application Ser. No. 07/651,436 filed Feb. 6, 1991, now abandoned.

FIELD OF THE INVENTION

This invention relates generally to anticonvulsant compounds and their use and specifically to substituted quinazolones that have anticonvulsant activity but limited or no sedative or hypnotic effect.

REFERENCES

Several publications are referenced herein by Arabic numerals within parenthesis. Full citations for these references may be found at the end of the specification immediately preceding the claims. The disclosures of these publications are hereby incorporated herein by reference in their entirety, unless otherwise noted.

BACKGROUND OF THE INVENTION

Gujral et al. (1,2) synthesized methaqualone (2-methyl-3-o-tolyl-4-quinazolone) and reported its sedative and hypnotic effect. In addition, it also possesses anticonvulsant, antispasmodic, local anesthetic, and weak antihistaminic properties (3). Unfortunately, the drug has high abuse potential and has been withdrawn from the market in the United States. It is represented by the following formula:

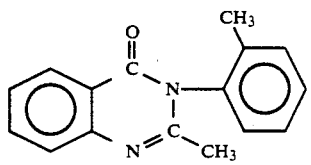

I

Numerous derivatives of methaqualone have been prepared. For example, 2-methyl-3-(2-trifluoromethylphenyl)-4-quinazolone was synthesized by Klosa and Starke. A comparison of this compound with methaqualone showed lower toxicity and better sedative effect (4). Some 4-oxo-3,4-dihydroquinazolines were prepared. These products exhibited various types of physiological activity (5). Anticonvulsant activity of 2-methyl-3-p-bromophenyl-4-quinazolone has been reported against pentylenetetrazol induced seizures (6). A number of derivatives of 2,3-substituted 4-quinazolones were synthesized. These compounds exhibited antiphlogistic, analgesic, antipyretic, and anticonvulsive effects (7). Bhaduri and Khanna synthesized 2,3-substituted 4-quinazolones and 8-aza quinazolones as potential CNS-depressants (8). Quinazolone hydrazides were synthesized, and these hydrazides exhibited some anticonvulsant activity (9, 10, 11). However, there is still a need for a safe anticonvulsant compound that has limited or no sedative or hypnotic effect.

In order to decrease the hypnotic property and abuse potential of methaqualone and retain the anticonvulsant activity, we attempted to decrease the lipid solubility of the drug by introducing a hetero nitrogen atom in the phenyl ring at position 3, at position 8, or at both positions. We also attempted to decrease lipid solubility by introducing a $NH_2$ group at position 6 or 7 of the quinazolone nucleus. Several other structural analogs of methaqualone were also prepared and evaluated for anticonvulsant activity. We discovered certain substituted quinazolones with anticonvulsant activity but with limited or no sedative or hypnotic effect.

SUMMARY OF THE INVENTION

It is an object of the invention to provide new anticonvulsant compounds that have limited or no sedative or hypnotic effect.

It is a further object of the invention to provide pharmaceutically acceptable salts of the new anticonvulsant compounds.

A still further object of the invention is to provide a composition for treating or preventing convulsions in mammals.

Another object of the invention is to provide methods of treating or preventing convulsions in mammals.

Yet another object of the invention is to provide methods for synthesizing the novel anticonvulsant compounds.

Still another object of the invention is to provide intermediate compounds useful in the synthesis of the anticonvulsant compounds of the invention.

Additional objects and advantages of the invention will be set forth in part in the description that follows, and in part will be obvious on the description, or may be learned by the practice of the invention. The objects and advantages of the invention will be attained by means of the instrumentalities and combinations particularly pointed out in the appended claims.

To achieve the objects and in accordance with the purpose of the invention, as embodied and broadly described herein, the present invention provides compounds represented by the following formula:

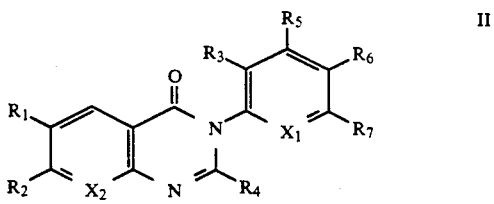

II in which $X_1$ is N, S, O, or CH, $X_2$ is N or CH, $R_1$ and $R_2$ are H, $NO_2$, or $NH_2$ except that when one of $R_1$ and $R_2$ is $NO_2$ or $NH_2$ the other is H, $R_3$ and $R_4$ are alkyl with 1-5 C atoms, and $R_5$, $R_6$, and $R_7$ are H or halogen, provided that when $X_1$ is N, S, or O, $X_2$ is CH. The invention also includes pharmaceutically acceptable salts of these compounds.

In a preferred embodiment, $X_1$ is N. When $X_1$ is N, preferably $R_3$ and $R_4$ are methyl, and $R_5$, $R_6$, and $R_7$ are H.

In alternative preferred embodiment, one of $R_1$ and $R_2$ is $NO_2$ or $NH_2$. In this case, preferably $X_1$ is N or CH, $R_3$ and $R_4$ are methyl, and $R_5$, $R_6$, and $R_7$ are H.

It has been found that the compounds of the invention and the physiologically acceptable acid addition salts have valuable pharmacological properties. In particular, they have anticonvulsant activity with limited or no sedative or hypnotic effect. Thus, the compounds, the acid addition salts, and compositions containing the compounds or salts in a pharmaceutically acceptable carrier are useful for treating or preventing convulsions in mammals in general and humans in particular.

The compounds of the invention are prepared in one of two ways. Where both $R_1$ and $R_2$ are H or one of $R_1$ and $R_2$ is $NO_2$, the appropriate substituted anthranilic acid is reacted with the appropriate anhydride to produce an anthranil intermediate. This compound is then reacted with the appropriate aromatic amine to produce the desired compound of the invention.

Where one of $R_1$ and $R_2$ of the desired quinazolone is $NH_2$, the appropriate quinazolone is prepared according to the previous paragraph, with an $NO_2$ group in the desired position, and the compound is then reacted with the appropriate reducing agent to reduce the $NO_2$ group to a $NH_2$ group.

Having the anticonvulsant substituted quinazolones compounds of the invention, a person skilled in the art can prepare $N^1$-oxide derivatives by reacting the compound with the appropriate oxidizing agent to oxidize the nitrogen in the 1-position.

DETAILED DESCRIPTION OF THE INVENTION

Reference will now be made in detail to the presently preferred embodiments of the invention, which, together with the following examples, serve to explain the principles of the invention.

The invention relates to anticonvulsant substituted quinazolones represented by Formula II and their physiologically acceptable acid addition salts. In one preferred embodiment of the invention, $X_1$ is nitrogen, sulfur, or oxygen. Preferably, $X_1$ is N or S, and most preferably it is N. When $X_1$ is N, S, or O, $X_2$ is CH.

In another preferred embodiment, one of $R_1$ and $R_2$ is $NO_2$ or $NH_2$. Preferably, one of $R_1$ and $R_2$ is $NH_2$, and the other is H.

In another preferred embodiment of the invention, $R_3$ and $R_4$ are alkyl containing 1-3 carbon atoms. Preferably, at least one of $R_3$ or $R_4$ is methyl. Most preferably, $R_3$ and $R_4$ are both methyl.

In another preferred embodiment of the invention, one or more of $R_5$, $R_6$, and $R_7$ are halogen.

In a particularly preferred embodiment, $X_1$ is N, $X_2$ is CH, and one of $R_1$ and $R_2$ is $NO_2$ or $NH_2$. Preferably, one of $R_1$ and $R_2$ is $NH_2$, and the other is H. In this case, it is also preferred that $R_3$ and $R_4$ are methyl and further that $R_5$, $R_6$, and $R_7$ are H.

In another particularly preferred embodiment of the invention, $X_1$ is N, $X_2$ is CH, and $R_1$ and $R_2$ are H. Most preferably, $R_3$ and $R_4$ are methyl and $R_5$-$R_7$ are H, which provides the especially preferred compound 2-methyl-3-(3-methyl-2-pyridyl)-4-quinazolone.

In another particularly preferred embodiment of the invention, $X_1$ in Formula II is CH, $X_2$ is CH, and one of $R_1$ and $R_2$ is $NO_2$ or $NH_2$. Most preferably, one of $R_1$ or $R_2$ is $NH_2$ and the other is H. In this case, $R_3$ and $R_4$ are preferably methyl, and $R_5$, $R_6$, and $R_7$ are H. Thus, another especially preferred compound of the invention is 2-methyl-3-o-tolyl-7-amino-4-quinazolone.

The compounds of the invention are prepared according to the following scheme:

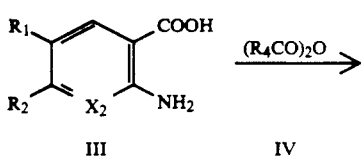

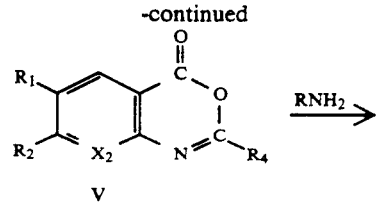

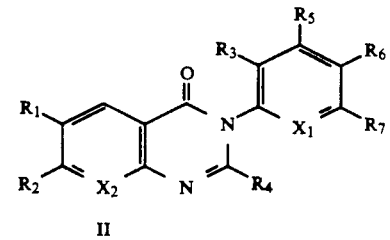

This scheme is a modification of the scheme for synthesizing methaqualone, which is disclosed in references 1 and 2.

In particular, a substituted anthranilic acid represented by Formula III above is reacted with an anhyride represented by the Formula IV to prepare an anthranil precursor represented by Formula V. In these formulas, both $R_1$ and $R_2$ are H or one is $NO_2$ and the other is H. $R_4$ is alkyl with 1-5 carbon atoms. Preferably, the substituted anthranilic acid is refluxed in the presence of the anhyride under conditions readily determinable by persons skilled in the art, given the teachings contained therein.

The anthranil intermediate is then reacted with an aromatic amine represented by the following formula (and shown as $RNH_2$ above):

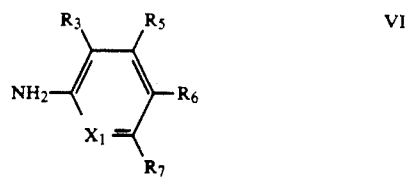

This produces the substituted quinazolones of the invention, which are recovered by known techniques. Preferably, the recovered compounds are recrystallized one or more times to enhance their purity.

Where $R_1$ or $R_2$ in Formula II is $NH_2$, a somewhat different synthesis is preferred. In particular, the desired substituted quinazolone is prepared according to the above scheme where one of $R_1$ and $R_2$ is $NO_2$ and the other is H. The $NO_2$ group is then reduced to $NH_2$ through the application of known reduction techniques and under reaction conditions that will be readily determinable to persons skilled in the art, given the teachings contained herein. Preferably, such reduction is accomplished by reacting the compound with a reducing agent, most preferably a mixture of iron and ammonium chloride.

It has been reported that methaqualone is metabolized in the body to the the $N^1$-oxide of the compound (3). Accordingly, it is to be expected that the compounds of the inventions will be active in the mammalian body as $N^1$-oxide derivatives of the compounds previously defined above. Thus, the invention also relates to $N^1$-oxide derivatives of the compounds of the invention. Such compounds have the following formula:

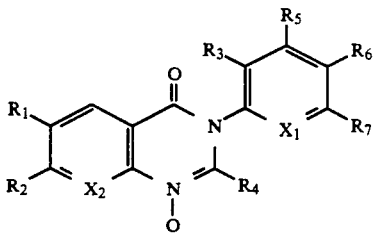

wherein $X_1$, $X_2$, and $R_1$–$R_7$ are as previously defined.

Such compounds may be produced through the application of known techniques for oxidizing the nitrogen atom in compounds similar to the claimed compounds by a person skilled in the art without undue experimentation, once given the teachings contained herein. Preferably, the compounds of Formula II are refluxed with hydrogen peroxide under reaction conditions readily determinable by persons skilled in the art, given the teachings contained herein, for a sufficient time to produce the compounds of Formula VII.

The compounds of the invention (including the $N^1$-oxide derivatives) are useful for treating or preventing convulsions in mammals. The compounds or their acid addition pharmaceutically acceptable salts made be administered directly. Preferably, such compounds or salts are in admixture with a pharmaceutically acceptable carrier, providing a composition for treating or preventing convulsions in mammals.

The preferred animal host is any animal that may be subject to convulsions for which treatment or prevention is desired. These include, but are not limited to, humans and other primates, dogs, cats, cattle, swine, and horses. Preferably, the compounds and compositions are administered to humans.

The pharmaceutically acceptable acid addition salts of this invention can be prepared by standard methods known in the art, employing those acids of sufficient acidity to form acid addition salts with the $N^1$ or $N^1$-oxide oxygen of the compounds of this invention. These include salts derived from inorganic acids, such as hydrochloric acid, nitric acid, phosphoric acid, sulfuric acid, hydrobromic acid, hydriodic acid, phosphorous acid, and the like, as well as salts derived from organic acids, such as aliphatic mono- and di-carboxylic acids, phenyl-substituted alkanoic acids, hydroxy-alkanoic and -alkanedioic acids, aromatic acids, aliphatic, and aromatic sulfonic acids. Such pharmaceutically acceptable salts thus include the sulfate, metaphosphate, pyrophosphate, chloride, bromide, iodide, fluoride, oxalate, maleate, benzene-sulfonate, toluenesulfonate, chlorobenzenesulfonate, methanesulfonate, propanesulfonate, naphthalene-1-sulfonate, naphthalene-2-sulfonate salts, and the like. The preferred salts are those derived from inorganic acids, especially hydrochloric acid.

The compounds of the invention may be administered as an anticonvulsant agent by various routes, including oral, parenteral rectal, transdermal, subcutaneous, intravenous, intramuscular, or intranasal routes. The preferred routes are oral and parenteral. They are usually employed in the form of a pharmaceutical composition. The invention includes a pharmaceutical composition comprising from about 1% to about 95% by weight of the compounds, or a pharmaceutically acceptable acid addition salt thereof, associated with a pharmaceutically acceptable carrier.

In making the compositions of the present invention, the active ingredient will usually be mixed with a carrier, or diluted by a carrier, or enclosed within a carrier which may be in the form of a capsule, sachet, paper, or other container. When the carrier serves as a diluent, it may be a solid, semi-solid, or liquid material which acts as a vehicle, excipient, or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compounds, soft and hard gelatin capsules, suppositories, sterile injectable solutions, and sterile packaged powders.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxbenzoates, talc, magnesium stearate, and mineral oil. The formulations can additionally include lubricating agents, wetting agents, emulsifying and suspending agents, preserving agents, sweetening agents, flavoring agents, or other active ingredients. The compositions of the invention may be formulated so as to provide quick, sustained, or delayed release of the active ingredient after administration to the patient.

The compositions will be preferably formulated in a unit dosage form, each dosage containing from about 50 to about 200 mg, preferably about 75 to about 150 mg, and most preferably about 80 to about 100 mg of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

The compounds are effective over a wide dosage range. For example, dosages per day will normally fall within the range of about 2 to about 8 mg/kg of body weight. In the treatment of adult humans, the range of about 1 to 2 mg/kg, in single or divided doses, is preferred. However, it will be understood that the amount of the compound actually administered will be determined by a physician or other person skilled in the art, in the light of the relevant circumstances, including the condition to be treated, the chosen route of administration, the age, weight, and response of the individual patient, the severity of the patient's symptoms, and the specific anticonvulsant substituted quinazolone or $N^1$-oxide derivative selected for use.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In such cases, either the reactions can be successfully performed by conventional modifications known to those skilled in the art, e.g., by appropriate protection of interfering groups, by changing to alternative conventional reagents, by routine modification of reaction conditions, etc., or other reactions disclosed herein or otherwise conventional, will be applicable to the preparation of the corresponding compounds of this invention. In all the preparative methods, all starting materials are known or readily preparable from known starting materials.

It is to be understood that the application of the teachings of the present invention to a specific problem or environment will be within the capabilities of one having ordinary skill in the art in light of the teachings contained herein. Examples of the products of the present invention and processes for their preparation and use appear in the following examples.

EXAMPLE 1

Preparation of Acetanthranils

Acetanthranils were prepared by refluxing substituted anthranilic acids (0.27 mole) in acetic anhydride (200 ml) for 2 hours. Acetic anhydride was removed in vacuo, and the residues were recrystallized from benzene.

8-Azaacetanthranil was prepared by refluxing 2-aminonicotinic acid (0.1 mole) in acetic anhydride (50 ml) for 2 hours. Acetic anhydride was removed under reduced pressure, and the solid obtained was recrystallized from benzene.

Various anthranils synthesized are listed in Table 1.

EXAMPLE 2

Preparation of Substituted Quinazolones

Substituted quinazolones were prepared by heating equimolar proportions of appropriate primary amine and anthranil at a low flame. The jelly-like mass obtained on cooling was washed with ether. The solid separated out and was filtered and recrystallized from suitable solvents. All the quinazolones synthesized are listed in Table 2. Details about the sythesis of the most active compounds are found in Examples 3 and 4.

EXAMPLE 3

2-Methyl-3-(3-methyl-2-pyridyl)-4-quinazolone (compound no. 2)

Acetanthranil (4.5 g, 0.028 mole) was mixed with 2-amino-3-picoline (2.7 g, 0.025 mole) and the mixture was heated in an erlenmeyer flask, first at low heat and then at high heat over an open flame. The product was washed with ether and recrystallized from ethanol/water mixture. The yield was 3.7 g (58%), mp 135°–137° C.

EXAMPLE 4

2-Methyl-3-o-tolyl-7-amino-4-quinazolone (compound no. 14)

This compound was prepared from 2-methyl-3-o-tolyl-7-nitro-4-quinazolone, which was prepared as follows. 7-nitro-acetanthranil (2.1 g, 0.011 mole) was mixed with o-toluidine (1.1 g, 0.010 mole) and heated in an erlenmeyer flask, first over a low flame and then over a high flame to complete the reaction. On cooling overnight, the reaction mixture solidified. The solid mass was stirred and broken up after the addition of ether. Suction filtration yielded 2.7 g (98%), mp 183°–186° C. After recrystallization from ethanol, the yield was 2.5 g (91%), mp 181°–183° C.

To a mixture of 2.0 g of iron powder (reduced) and 1.0 g 2-methyl-3-o-tolyl-7-nitro-4-quinazolone (0.0036 mole) in a test tube (8"×1") was added 2 ml of 1 N ammonium chloride and 8 ml ethanol. The mixture was warmed gently in a water bath until the initial vigorous reaction had subsided. The test tube was then heated in the water bath until the solvents had evaporated (about 1 hr). The residue was extracted with four 10 ml portions of benzene, and the extracts were suction-filtered. The filtrate was heated with stirring, and n-hexane was added to cloudiness. The suspension was placed in the refrigerator overnight, and the white crystals were removed by suction-filtration. The yield was 0.9 g (100%), mp 211°–212° C.

EXAMPLE 5

2-Propyl-3-(2-methyl-4-chloro-phenyl)-4-quinazolone

This compound is prepared from butyranthranil, which is prepared as follows. Anthranilic acid (37.0 g, 0.270 mole) is refluxed with 200 ml butyric anhydride for two hours. The solvent is removed in vacuo (15 mm) with magnetic bar stirring, and the residue is dissolved in 100 ml benzene, filtered, and transferred to a beaker. The reaction flask is washed with 50 ml hot benzene. The washing is filtered and added to the benzene in the beaker. The benzene solution is concentrated to 100 ml by heating and allowed to cool to room temperature. The mixture is placed in the refrigerator overnight, then ground up in a mortar and pestle and suction-filtered. The crystals are air-dried and weighed.

Butyranthranil (5.3 g, 0.028 mole) is mixed with 2-methyl-4-chloro-aniline (3.6 g, 0.025 mole), and the mixture is heated in an erlenmeyer flask over an open flame, first at low heat and then at high heat to complete the reaction. The product is washed with ether and recrystallized from the appropriate solvent.

EXAMPLE 6

Determination of anticonvulsant activity

Anticonvulsant activity was determined in male mice (Swiss-Webster, 20–25 g). The mice were divided in groups of 10, keeping the group weights equal as far as possible. The quinazolones shown in Table 2 as well as methaqualone were injected ip (100 mg/kg) in a 5% aqueous suspension of gum acacia to one group of 10 animals. One hour after the administration of quinazolones, the mice were injected with pentylenetetrazol (90 mg/kg) sc under the loose skin of the back. This dose of pentylenetetrazol has been shown to produce convulsions in all untreated mice. The mice were then observed for the following 60 minutes for the occurrence of seizures. One episode of clonic spasm which persisted for a minimum period of 5 seconds was considered a threshold convulsion. Transient intermittent jerks or tremulousness were not taken into account. Animals devoid of even a threshold convulsion during the period of 60 minutes were considered protected. The number of animals protected in each group was recorded, and the anticonvulsant activity of these quinazolones was represented as percent protection. Mortality was recorded 24 hours after the pentylenetetrazol injection. After the injection of test compounds, behavioral observations were also made. Data are given in Table 3. The results show that compound no. 2 and compound no. 14 exhibited 100% protection against pentylenetetrazol seizures and that they did not exhibit any toxicity at the effective dosage.

EXAMPLE 7

Dose Response, Time Response, and Approximate $LD_{50}$

Dose response and time response studies were performed with compound no. 2 by injecting it into a group of 10 male Swiss-Webster mice. In addition, a group of 10 male ICR mice were injected with different dosages of compound no. 2 to determine the approximate $LD_{50}$. The animals were observed for 24 hours, and the $LD_{50}$ was calculated. Results are given in Table 4.

In addition, compound no. 2 was also tested against Maximal Electric Shock (MES) seizure. Compound no. 2 exhibited 100% protection against MES at 30 mg/kg ip in mice.

EXAMPLE 8

Anticonvulsant Effect of Compound No. 2 in Rats

Compound No. 2 was also tested in rats. Four rats were treated with compound no. 2 at a dosage of 50 mg/kg orally. Anticonvulsant effects of compound no. 2 were observed at different time periods against both maximal electric shock seizures (MES) and pentylenetetrazol-induced seizure. The toxic symptoms were also observed. Data are given in Table 5. It can be seen from this table that compound no. 2 protected against both MES and pentylenetetrazol-induced seizure at all time periods without exhibiting any toxic symptoms.

Maximal electroshock seizures were elicited with a 60 cycle alternating current of 50mA intensity (5-7 times that necessary to elicit minimal electroshock seizures) delivered for 0.2 seconds via corneal electrodes. A drop of 0.9% saline was instilled in the eye prior to application of the electrodes in order to prevent the death of the animal. Abolition of the hind limb tonic extension component of the seizure was defined as protection.

As it appears from the results in Examples 6, 7, and 8, compounds 2 and 14 are effective anticonvulsants with higher therapeutic indices than methaqualone, indicating a wider safety margin.

TABLE 1

Substituted Anthranils

| $R_1$ | $R_2$ | X | m.p. °C. | Recrystallization solvent |
|---|---|---|---|---|
| H | H | CH | 78-80 | Benzene |
| H | H | N | 174-176 | Benzene |
| $NO_2$ | H | CH | 156-160 | Benzene |
| H | $NO_2$ | CH | 139-142 | Benzene |

TABLE 2

Substituted Quinazolones*

| Compound No. | $R_1$ | $R_2$ | $R_3$ | $X_1$ | $X_2$ | m.p. °C. | Recrystallization solvent |
|---|---|---|---|---|---|---|---|
| 2 | H | H | $CH_3$ | N | CH | 135-137 | Ethanol-water |
| 3 | H | H | $CH_3$ | CH | N | 148-150 | Ethanol |
| 4 | H | H | $CH_3$ | N | N | 252-253 | Ethanol |
| 5** | H | H | $CH_3$ | $CH_2$ | CH | 160-162 | Ethanol |
| 6 | H | H | COOH | CH | CH | 244-246 | Ethanol-water |
| 7 | H | H | $NO_2$ | CH | CH | 155-165 | Ethanol-water |
| 8 | H | H | $NO_2$ | N | CH | 152-160 | Ethanol |
| 9 | $NO_2$ | H | $CH_3$ | CH | CH | 181-183 | Ethanol |
| 10 | $NH_2$ | H | $CH_3$ | CH | CH | 221-223 | Benzene-n-hexane |
| 11 | $NO_2$ | H | $CH_3$ | N | CH | 220-221 | Ethanol |
| 12 | $NH_2$ | H | $CH_3$ | N | CH | 250-253 | Benzene-n-hexane |
| 13 | H | $NO_2$ | $CH_3$ | CH | CH | 181-183 | Ethanol |
| 14 | H | $NH_2$ | $CH_3$ | CH | CH | 211-212 | Benzene-n-hexane |
| 15 | H | $NO_2$ | $CH_3$ | N | CH | 156-158 | Ethanol |
| 16 | H | $NH_2$ | $CH_3$ | N | CH | 201-203 | Benzene-n-hexane |

*All the compounds were characterized by sharp melting points and elemental analyses (C, H, & N within ±0.5%).
**In this compound, the ring at position 3 is saturated (cyclohexyl).

TABLE 3

Anticonvulsant Activity and gross CNS effects of Substituted quinazolones

| Compound No. | Percent Protection | 24 Hour Mortality | Behavioral Observations |
|---|---|---|---|
| 1 (Methaqualone) | 100 | 0 | deep hynosis |
| 2 | 100 | 0 | mild sedation |
| 3 | 10 | 0 | none |
| 4 | 0 | 80 | none |
| 5 | 20 | 40 | none |
| 6 | 0 | 30 | none |
| 7 | 10 | 40 | none |
| 8 | 0 | 50 | none |
| 10 | 40 | 30 | none |
| 12 | 30 | 50 | none |
| 14 | 100 | 0 | none |
| 16 | 40 | 40 | none |

TABLE 4

Anticonvulsant effect of 2-methyl 3-(3-methyl-2-pyridyl)-4-quinazolone

Dose Response*

| Dosage mg/kg, i.p. | Percent Protection against pentylenetetrazol (90 mg/kg, s.c.) given 1 hour after the injection of the test compound. |
|---|---|
| 40 | 20 |
| 60 | 80 |
| 80 | 90 |
| 100 | 100 |

Time Response**

| Time after the injection of the test compound (hr) | Percent Protection against pentylenetetrazol (90 mg/kg s.c.) |
|---|---|
| 1 | 100 |
| 2 | 60 |
| 3 | 0 |
| 4 | 0 |

*Group of 10 male mice (Swiss-Webster, 20-25 g) were used for each time period. The test compound was given in 5% aqueous gum acacia suspension.
**Group of 10 male mice (Swiss-Webster, 20-25 g) were used for each time period. The test compound was given at a dosage of 100 mg/kg, i.p. in 5% aqueous gum acacia suspension.

Approximate $LD_{50}$

Approximate $LD_{50}$ was determined in male ICR mice. Approximate $LD_{50}$ was found to be about 1000 mg/kg, i.p.

TABLE 5
Anticonvulsant Effect of Compound No. 2*

| Time after oral administration of Compound no. 2 (Hr.) | Percent protection against pentylenetetrazol | Percent protection against MES | Toxicity in percent rats |
|---|---|---|---|
| 0.25 | 33.3** | 75 | 0 |
| 0.5 | 75 | 50 | 0 |
| 1 | 25 | 75 | 0 |
| 2 | 0.1 | 50 | 0 |
| 4 | 25 | 25 | 0 |

*Group of four rats were used for each time period. Compound no. 2 was given at a dosage of 50 mg/kg orally in 0.5% methylcellulose suspension.
**Three rats were used.

REFERENCES

1. Gujral, M.L., Saxena, P.N. and Tewari, R.S., *Ind. J. Med. Res.* 43, 637 (1955).
2. Gujral, M.L., Sareen, K.N., and Kohli, R.P., *Ind. J. Med. Res.* 45, 207 (1957).
3. Harvey, S.C. in Goodman and Gilman's *The Pharmacological Basis of Therapeutics* (eds. Gilman, Goodman, Ral, Murad), p. 365, seventh edition, Macmillan (1985).
4. Klosa, J. and Starke, H., Ger (East) patent 32,296 (Cl C 07d2), Nov. 25, 1964.
5. Kaupmann, W. and Funke, S., Ger patent 1,168,435 (Cl. Co7d) Apr. 23, 1964.
6. Bianchi, C., and David, A., *J. Pharm. Pharmacol.* 12, 501 (1960).
7. Kretzschmar, E., *Pharmazie*, 35, 253 (1980).
8. Bhaduri, A.P. and Khanna, N.M., *Ind. J. Chem.* 4, 447 (1966).
9. Kohli, R.P., Gupta, T.K., Parmar, S.S., and Arara, R.C., *Jap. J. Pharmacol.* 17, 409 (1967).
10. Dwivedi, C. and Parmar, S.S., *Curr. Sci.* 41, 487 (1972).
11. Dwivedi, C., Misra, R.S., Chaudhari, A., and Parmar, S.S., *J. Nat. Med. Assoc.* 72, 953 (1980).

We claim:

1. An anticonvulsant composition with limited or no sedative or hypnotic effect for treating or preventing convulsions in mammals comprising, in a pharmaceutically acceptable carrier, an amount of the compound represented by the following formula or pharmaceutically acceptable salts of said compound effective for said treatment or prevention:

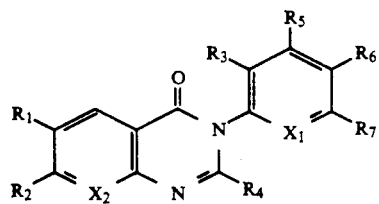

wherein $X_1$ is N or CH, $X_2$ is N or CH, $R_1$ and $R_2$ are H, $NO_2$, or $NH_2$ except that when one of $R_1$ and $R_2$ is $NO_2$ or $NH_2$ the other is H, $R_3$ and $R_4$ are alkyl with 1-5 C atoms, and $R_5$, $R_6$, and $R_7$ are H or halogen, provided that when $X_1$ is N, $X_2$ is CH.

2. The composition of claim 1 wherein $X_1$ is N, $X_2$ is CH, and $R_1$ and $R_2$ are H or $NH_2$.

3. The composition of claim 2 wherein $R_2$ is $NH_2$.

4. The composition of claim 2 wherein $R_1$ and $R_2$ are H, $R_3$ and $R_4$ are methyl, and $R_5$, $R_6$, and $R_7$ are H.

5. The composition of claim 1 wherein $X_1$ is CH and $R_1$ and $R_2$ are H or $NH_2$.

6. The composition of claim 5 wherein $R_2$ is $NH_2$.

7. The composition of claim 6 wherein $X_2$ is CH, $R_3$ and $R_4$ are methyl, and $R_5$, $R_6$, and $R_7$ are H.

8. A method of treating or preventing convulsions in a mammal while causing limited or no sedative or hypnotic effect comprising administering to said mammal a pharmaceutically effective amount for said treatment or prevention of the compound represented by the following formula or pharmaceutically acceptable salts of said compound:

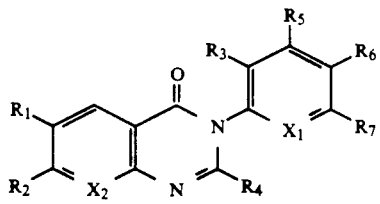

wherein $X_1$ is N or CH, $X_2$ is N or CH, $R_1$ and $R_2$ are H, $NO_2$, or $NH_2$ except that when one of $R_1$ and $R_2$ is $NO_2$ or $NH_2$ the other is H, $R_3$ and $R_4$ are alkyl with 1-5 C atoms, and $R_5$, $R_6$, and $R_7$ are H or halogen, provided that when $X_1$ is N, $X_2$ is CH.

9. The method of claim 8 wherein approximately 2 mg to 8 mg of said compound or salt is administered per kilogram of body weight of said mammal.

10. The method of claim 9 wherein said compound or salt is administered orally or parenterally.

11. The method of claim 10 wherein said mammal is a human.

12. The method of claim 11 wherein $X_1$ in said formula is N, $X_2$ is CH, and $R_1$ and $R_2$ are H or $NH_2$.

13. The method of claim 12 wherein $R_2$ is $NH_2$.

14. The method of claim 12 wherein $R_1$ and $R_2$ are H, $R_3$ and $R_4$ are methyl, and $R_5$, $R_6$, and $R_7$ are H.

15. The method of claim 11 wherein $X_1$ in said formula is CH and $R_1$ and $R_2$ are H or $NH_2$.

16. The method of claim 15 wherein $R_2$ is $NH_2$.

17. The method of claim 16 wherein $X_2$ is CH, $R_3$ and $R_4$ are methyl, and $R_5$, $R_6$, and $R_7$ are H.

18. A method of treating or preventing convulsions in a mammal while causing limited or no sedative or hypnotic effect comprising administering a pharmaceutically effective amount of the composition of claim 1 to said mammal.

* * * * *